United States Patent
McCusker et al.

(10) Patent No.: US 8,672,667 B2
(45) Date of Patent: Mar. 18, 2014

(54) ELECTRICALLY INSULATIVE STRUCTURE HAVING HOLES FOR FEEDTHROUGHS

(75) Inventors: Desmond A. McCusker, Rozelle (AU); Mark Spalding, Quakers Hill (AU); Steven J. Berry, Mardi (AU); Nicholas C. K. Pawsey, North Ryde (AU); Steven Kennedy, Toukley (AU)

(73) Assignee: Cochlear Limited, Macquarie University, NSW (AU)

(*) Notice: Subject to any disclaimer, the term of this patent is extended or adjusted under 35 U.S.C. 154(b) by 664 days.

(21) Appl. No.: 12/669,793

(22) PCT Filed: Jul. 15, 2008

(86) PCT No.: PCT/AU2008/001030
§ 371 (c)(1),
(2), (4) Date: Jun. 14, 2010

(87) PCT Pub. No.: WO2009/009827
PCT Pub. Date: Jan. 22, 2009

(65) Prior Publication Data
US 2010/0326723 A1 Dec. 30, 2010

(30) Foreign Application Priority Data
Jul. 17, 2007 (AU) .................... 2007903878

(51) Int. Cl.
*B29C 45/34* (2006.01)
(52) U.S. Cl.
USPC ................ 425/443; 425/438; 425/555
(58) Field of Classification Search
USPC ......... 425/438, 441, 443, 468, 546, 555, 577; 249/176; 264/299
See application file for complete search history.

(56) References Cited

U.S. PATENT DOCUMENTS

| | | | |
|---|---|---|---|
| 1,948,875 A | 2/1934 | Beitling | |
| 2,824,306 A | 2/1958 | Pfaff et al. | |
| 3,166,104 A | 1/1965 | Foley et al. | |
| 3,271,625 A | 9/1966 | Caracciolo | |
| 3,429,788 A | 2/1969 | Parstorfer | |
| 3,467,990 A * | 9/1969 | Kutik et al. ............ | 425/589 |
| 3,478,424 A | 11/1969 | Meoni | |
| 3,497,947 A | 3/1970 | Ardezzone | |
| 4,101,899 A | 7/1978 | Jones, Jr. et al. | |
| 4,200,971 A | 5/1980 | Shimizu et al. | |
| 4,396,792 A | 8/1983 | Falk | |

(Continued)

FOREIGN PATENT DOCUMENTS

| | | |
|---|---|---|
| AU | 2009200093 B2 | 3/2011 |
| DE | 41 39 440 A1 | 6/1993 |

(Continued)

OTHER PUBLICATIONS

International Search Report. PCT/AU2008/001030. Mailed Sep. 17, 2008.

(Continued)

*Primary Examiner* — Yogendra Gupta
*Assistant Examiner* — Emmanuel S Luk
(74) *Attorney, Agent, or Firm* — Kilpatrick, Townsend & Stockton, LLP.

(57) ABSTRACT

Forming feedthrough device comprising an electrically insulative structure having holes extending there through. The holes have disposed therein conductive members around which the electrically insulative structure is hermetically sealed.

16 Claims, 5 Drawing Sheets

(56) References Cited

U.S. PATENT DOCUMENTS

| | | | |
|---|---|---|---|
| 4,602,637 A | 7/1986 | Elmqvist et al. | |
| 4,785,827 A | 11/1988 | Fischer | |
| 4,797,236 A * | 1/1989 | Kojima | 264/40.1 |
| 4,865,562 A | 9/1989 | Burg et al. | |
| 4,936,792 A | 6/1990 | Onoue et al. | |
| 5,041,019 A | 8/1991 | Sharp et al. | |
| 5,103,818 A | 4/1992 | Maston et al. | |
| 5,206,495 A | 4/1993 | Kreft | |
| 5,274,917 A | 1/1994 | Corbett, III et al. | |
| 5,282,841 A | 2/1994 | Szyszkowski | |
| 5,336,246 A | 8/1994 | Dantanarayana | |
| 5,409,362 A * | 4/1995 | Neu | 425/116 |
| 5,419,865 A * | 5/1995 | Ogata et al. | 264/328.1 |
| 5,462,408 A | 10/1995 | Coffy | |
| 5,596,797 A | 1/1997 | Bumsted | |
| 5,683,435 A | 11/1997 | Truex et al. | |
| 5,753,164 A * | 5/1998 | Ritchie et al. | 264/102 |
| 5,779,839 A | 7/1998 | Tuttle et al. | |
| 5,780,079 A * | 7/1998 | Lee | 425/577 |
| 5,782,645 A | 7/1998 | Stobie et al. | |
| 5,833,714 A | 11/1998 | Loeb | |
| 5,907,893 A | 6/1999 | Zadno-Azizi et al. | |
| 5,925,852 A | 7/1999 | Hinz et al. | |
| 5,967,841 A | 10/1999 | Bianca et al. | |
| 6,011,993 A | 1/2000 | Tziviskos et al. | |
| 6,052,623 A | 4/2000 | Fenner et al. | |
| 6,101,371 A | 8/2000 | Barber et al. | |
| 6,119,044 A | 9/2000 | Kuzma | |
| 6,133,072 A | 10/2000 | Fjelstad | |
| 6,179,659 B1 | 1/2001 | Moden | |
| 6,181,296 B1 | 1/2001 | Kulisan et al. | |
| 6,195,858 B1 | 3/2001 | Ferguson et al. | |
| 6,206,735 B1 | 3/2001 | Zanolli | |
| 6,219,247 B1 | 4/2001 | Haupt et al. | |
| 6,297,943 B1 | 10/2001 | Carson | |
| 6,308,744 B1 | 10/2001 | Becherucci et al. | |
| 6,336,269 B1 | 1/2002 | Eldridge et al. | |
| 6,364,654 B1 * | 4/2002 | Luther | 425/556 |
| 6,414,835 B1 | 7/2002 | Wolf et al. | |
| 6,421,569 B1 | 7/2002 | Treaba et al. | |
| 6,446,678 B1 | 9/2002 | Becherucci et al. | |
| 6,447,304 B1 | 9/2002 | Korsunsky et al. | |
| 6,501,437 B1 | 12/2002 | Gyorko et al. | |
| 6,505,073 B2 | 1/2003 | Gramse | |
| 6,517,476 B1 | 2/2003 | Bedoya et al. | |
| 6,552,655 B2 | 4/2003 | Barbulescu | |
| 6,638,121 B1 | 10/2003 | Walker et al. | |
| 6,704,994 B1 | 3/2004 | Gijs | |
| 6,721,602 B2 | 4/2004 | Engmark et al. | |
| 6,764,336 B2 | 7/2004 | Ma et al. | |
| 6,765,779 B2 | 7/2004 | Stevenson et al. | |
| 6,820,314 B2 | 11/2004 | Ferguson et al. | |
| 7,184,843 B1 | 2/2007 | Cohen | |
| 7,223,085 B2 * | 5/2007 | Puniello et al. | 425/116 |
| 7,300,268 B2 * | 11/2007 | Dooley et al. | 425/4 R |
| 7,337,974 B2 | 3/2008 | Caruana | |
| 7,396,265 B2 | 7/2008 | Darley et al. | |
| 7,503,758 B2 * | 3/2009 | Reis et al. | 425/12 |
| 7,950,134 B2 | 5/2011 | Ho et al. | |
| 7,988,507 B2 | 8/2011 | Darley et al. | |
| 7,996,982 B2 | 8/2011 | Darley et al. | |
| 8,016,586 B2 * | 9/2011 | Entezarian et al. | 425/468 |
| 2001/0039374 A1 | 11/2001 | Schulman | |
| 2003/0069613 A1 | 4/2003 | Kuzma et al. | |
| 2004/0164923 A1 | 8/2004 | Aisenbrey | |
| 2006/0085055 A1 | 4/2006 | Dadd et al. | |
| 2007/0031532 A1 * | 2/2007 | Chen | 425/555 |
| 2007/0053812 A1 * | 3/2007 | Kawai et al. | 422/243 |
| 2007/0126138 A1 * | 6/2007 | Dooley et al. | 264/46.4 |
| 2007/0128940 A1 | 6/2007 | Ho et al. | |
| 2009/0061127 A1 * | 3/2009 | Entezarian et al. | 428/34.4 |
| 2010/0019408 A1 * | 1/2010 | Kawai et al. | 264/156 |
| 2010/0207302 A1 * | 8/2010 | Ootera et al. | 264/478 |
| 2010/0292760 A1 | 11/2010 | Leigh et al. | |
| 2011/0300764 A1 | 12/2011 | Darley et al. | |

FOREIGN PATENT DOCUMENTS

| | | |
|---|---|---|
| EP | 1 547 207 B1 | 8/2011 |
| GB | 2 166 005 A | 4/1986 |
| GB | 2 288 028 A | 10/1995 |
| GB | 2 356 935 A | 6/2001 |
| JP | 63-274074 A | 11/1988 |
| JP | 2001-009841 A | 1/2001 |
| JP | 2001-052780 A | 2/2001 |
| JP | 2002-119435 A | 4/2002 |
| JP | 2003-317892 A | 11/2003 |
| WO | 02/03408 A2 | 1/2002 |
| WO | 02/089907 A1 | 11/2002 |
| WO | 2004/030159 | 4/2004 |
| WO | 2005/055363 A1 | 6/2005 |
| WO | 2006/081361 A2 | 8/2006 |
| WO | 2007/050212 A2 | 5/2007 |
| WO | 2009/009827 A1 | 1/2009 |

OTHER PUBLICATIONS

Japanese Application No. 2004-538572, Notice of Rejection mailed on Sep. 30, 2008, 7 Pages.
Derwent Abstract Accession No. 87-121639/17, SU 1256-122 A, Frunze Ty Azhelektro, Sep. 7, 1986.
Derwent Abstract Accession No. 93-376433/47, SU 1775803, Khak Aivation Inst., Nov. 15, 1992.
Australian Application No. 2003266816, Office Action mailed on Apr. 17, 2007, 2 Pages.
Australian Application No. 2009200093, Office Action mailed on May 19, 2010, 2 Pages.
Australian Application No. 2011201190, Office Action mailed on Oct. 7, 2011, 1 Page.
European Application No. 03747701.5, Supplementary Search Report mailed on Feb. 27, 2007, 3 Pages.
European Application No. 03747701.5, Communication Pursuant to Article 94(3) EPC mailed on Nov. 6, 2008, 5 Pages.
International Application No. PCT/AU03/01288, International Search Report mailed on Oct. 31, 2003, 5 Pages.
International Application No. PCT/AU08/001030, International Preliminary Report on Patentability mailed on Jan. 19, 2010, 5 Pages.
International Application No. PCT/AU08/001030, International Search report and Written Opinion mailed on Sep. 17, 2008, 6 Pages.
International Application No. PCT/AU2004/001726, International Preliminary Report on Patentability mailed on Nov. 23, 2005, 5 Pages.
International Application No. PCT/AU2004/001726, International Search Report and Written Opinion mailed on Mar. 18, 2005, 10 Pages.
International Application No. PCT/AU2008/000973, International Search Report mailed on Aug. 29, 2008, 5 Pages.
International Application No. PCT/US2008/083794, International Preliminary Report on Patentability mailed on Nov. 10, 2009, 7 Pages.
International Application No. PCT/US2008/083794, International Search Report and Written Opinion mailed on Jan. 22, 2009, 5 Pages.
International Application No. PCTAU2003001288, International Preliminary Examination Report mailed on Jan. 18, 2005, 5 Pages.
Petersen, "Silicon as a Mechanical Material", Proceedings of the IEEE, vol. 70, No. 5, May 1982, pp. 420-457.
Rousche et al., "Flexible Polyimide-Based Intracortical Electrode Arrays with Bioactive Capability", IEEE Transactions on Biomedical Engineering, vol. 48, No. 3, Mar. 2001, 11 Pages.
Ziaie et al., "A Hermetic Glass-Silicon Micropackage with High-Density On-Chip Feedthroughs for Sensors and Actuators", Microelectromechanical Systems Journal, vol. 5, Issue 3, Sep. 1996, pp. 166-179.

* cited by examiner

ELECTRICALLY INSULATIVE STRUCTURE HAVING HOLES FOR FEEDTHROUGHS

CROSS-REFERENCE TO RELATED APPLICATIONS

This application is a national stage application under 35 USC §371(c) of International Application No. PCT/AU2008/001030, entitled "METHOD AND APPARATUS FOR FORMING AN ELECTRICALLY INSULATING STRUCTURE HAVING HOLES FOR FEEDTHROUGHS," filed on Jul. 15, 2008, which claims priority from Australian Patent Application No. 2007903878, filed on Jul. 17, 2007. The entire disclosure and contents of the above applications are hereby incorporated by reference herein.

BACKGROUND

1. Field of the Invention

The present invention relates generally to feedthroughs, and more particularly to, forming an electrically insulative structure having holes for feedthroughs.

2. Related Art

As used herein, a 'feedthrough' is an electrically conductive path extending through an insulative member, and which has portions accessible at each side of the insulative member. The electrically conductive path may extend from the interior of a hermetically sealed container or housing on one side of the insulative member, to an external location outside the container or housing on the other side of the insulative member. Typically, a conductive path is provided by an electrically conductive pin or rod, which is electrically insulated from the container or housing by an electrically insulating body surrounding the pin. As such, a feedthrough allows one or more electrical connections to be made between electronic circuitry or other components within a hermetically sealed container or housing and components outside the housing, while protecting the circuitry or components from any damage or malfunction that may result from exposure to the surrounding environment. A structure comprising a collection of one or more feedthroughs is sometimes referred to herein as a 'feedthrough device.'

There are many applications for feedthrough devices. One exemplary application is in electrical devices for implantation in a patient's body to provide therapy to the patient, such as cardiac pacemakers, defibrillators and cochlear implants, collectively and generally referred to herein as implantable medical devices. As the environment of living tissue and body fluids is relatively corrosive and devices may contain materials which may be detrimental if exposed to the patient, a hermetic feedthrough device is used to provide a barrier between the electronic components of the medical device and the external corrosive environment of the human body. With implantable medical devices in particular, it is beneficial that the hermetic seal of the device be physically rugged and long lasting. For this reason, stringent requirements are imposed on the hermeticity of an implanted device, typically requiring a seal that provides a leakage rate of approximately less than $10^{-8}$ cc/sec.

As such, conventional feedthrough devices used in implantable medical devices typically consist of a ceramic or glass bead that is bonded chemically at its perimeter through brazing or the use of oxides, and/or mechanically bonded through compression, to the walls of the sealed package. A suitable wire or other conductor passes through the center of the bead, and this wire or conductor must also be sealed to the bead through chemical bonds and/or mechanical compression. Such feedthroughs are typically cylindrical and the wire(s) or conductor(s) mounted within the bead are centered or mounted in a uniform pattern, centrally within the bead. Other materials and processes are known for making conventional feedthroughs for implantable medical devices rely, for example, on use of aluminum oxide ceramic and binders.

One of the conventional processes for making a feedthrough consists of pre-drilling holes in a sintered ceramic plate and then forcing electrical conductive pins through the holes. Examples of such processes are disclosed in U.S. Pat. No. 5,046,242. While useful, this method is tedious, slow, does not necessarily guarantee a hermetic seal, and generally results in unsatisfactory leakage rates and yields. Furthermore, it has been found that drill bits wear quickly when used on ceramics due to the abrasive nature of the ceramics. Thus, to meet required tolerances, drill bits typically need to be replaced often. Also, the build-up of stress around punched or drilled holes can result in subsequent cracking of the sintered ceramic.

Another conventional method for making a feedthrough involves inserting the conductive pins into an unsintered ceramic plate then curing the assembly by firing to achieve a hermetic seal. A major disadvantage of this process is that, historically such processes were required to be performed by hand. Such a manual method of manufacture can lead to inaccuracies and may be time consuming, expensive and labor intensive. Moreover, feedthroughs resulting from such a process do not necessarily have precisely positioned electrical conductors, with the position of the conductors being greatly dependent upon the process itself. Furthermore, as the conductors are typically wires being of a general cylindrical shape and configuration, the size and shape of the accessible portions of the conductor are generally the same as the conductor embedded in the insulative material.

As implantable medical devices continue to develop and become thinner, smaller and more electronically sophisticated, the requirements of the feedthrough have also increased. For example, in certain cochlear implants, where there are 22-24 electrodes, there may be a need for 22-24 conductive pins passing through the feedthrough device. As the desire for more electrodes and smaller feedthrough devices increases, the demands placed upon the design of the traditional feedthrough also increases. The problems in fabricating feedthrough devices on a large scale are significant, especially when one considers the relatively high degree of labor intensity and specialization of current fabricating methods.

While the above described conventional feedthrough devices and fabrication methods have proven successful, it is a relatively slow and labor intensive process to manufacture such devices. These methods of manufacture of the feedthrough devices also presents limitations as to the construction of the feedthrough devices.

US Patent Publication No. 2006/0141861, by the present applicant, discloses various embodiments of methods for forming a feedthrough device. In the embodiment illustrated in FIG. 26 of this US publication, an electrically insulating structure having holes for feedthroughs is formed by powder injection molding (PIM). The mold includes a pair of opposed mold plates, with one of the plates carrying a number of pins and the other plate having recesses which receive the pins. The plates are slowly moved apart to expose a partial cavity, into which hot feedstock is injected. The feedstock is injected in the partial cavity around the exposed portions of the pins. The process of moving the plates apart and injecting feedstock into the further exposed cavity continues until the cavity is fully molded. Once this process is completed, the molded structure is ejected, the molded structure having holes formed therethrough where the pins were located. The holes then allow feedthrough conductors to be arranged through the molded structure. The content of US Patent Publication No. 2006/0141861 is hereby incorporated by reference herein.

SUMMARY

In one aspect of the present invention, an apparatus for forming an electrically insulative structure having holes for feedthroughs is provided. The apparatus comprises: a housing defining a cavity having first and second ends; an injection nozzle disposed at the first end of the cavity configured to inject moldable material into the cavity; a plurality of pins extending through the cavity from the second to the first end; a cavity member extending across the cavity so as to form a sub-cavity between the cavity member and the first end of the cavity into which the moldable material is injected, the cavity member having a plurality holes through which the pins extend; wherein the member is initially positioned such that the member is adjacent the first end, and wherein the member is configured to move, relative to the pins and the housing, away from the first end along an axis to increase the volume of the sub-cavity as the moldable material is injected.

In another aspect of the present invention, a method of forming a feedthrough device through the use of a mold apparatus comprising a housing defining a cavity having first and second ends, an injection nozzle disposed at the first end of the cavity, a plurality of pins extending through the cavity along the axis, and a cavity member extending across the cavity so as to form a sub-cavity between the cavity member and the first end of the cavity into which the moldable material is injected, the cavity member having a plurality holes through which the pins extend is provided. The method comprises: biasing the cavity member such that the member is adjacent the first end of the cavity; and injecting moldable electrically insulative material into the cavity via the nozzle such that the cavity member moves, relative to the pins and the housing, along an axis away from the first end to increase the volume of the sub-cavity as the moldable material is injected.

BRIEF DESCRIPTION OF THE DRAWINGS

Embodiments of the present invention are described below with reference to the attached drawings, in which.

DETAILED DESCRIPTION

Embodiments of the present invention are generally apparatus and methods for forming an insulative structure usable as a component of a feedthrough device. Subsequent to the molding, hermetically sealed feedthroughs are formed in the holes to form a feedthrough device.

Figure 1:
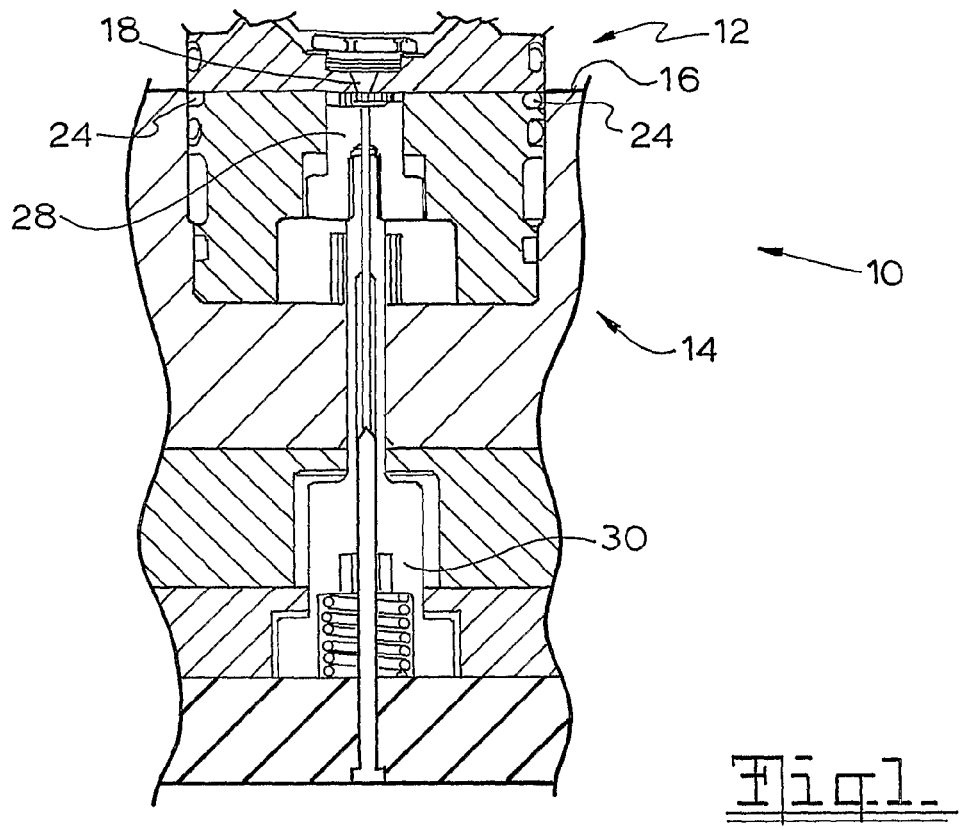
FIG. 1 is a cross-sectional view of an exemplary molding apparatus, in accordance with embodiments of the present invention.
Figure 2:
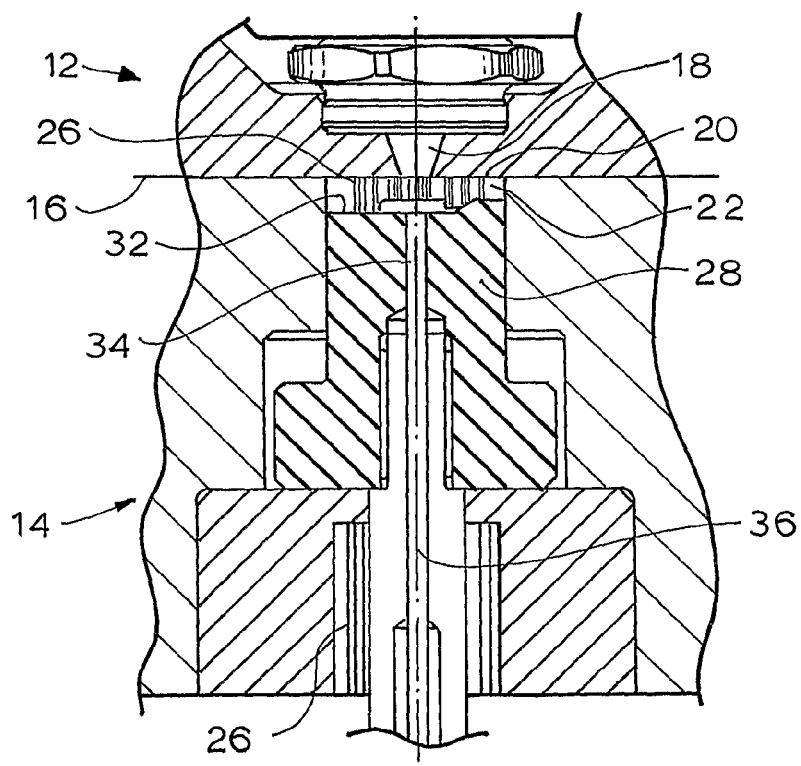
FIG. 2 is cross-sectional view of a section of the molding apparatus of FIG. 1, in accordance with embodiments of the present invention.
Figure 3:
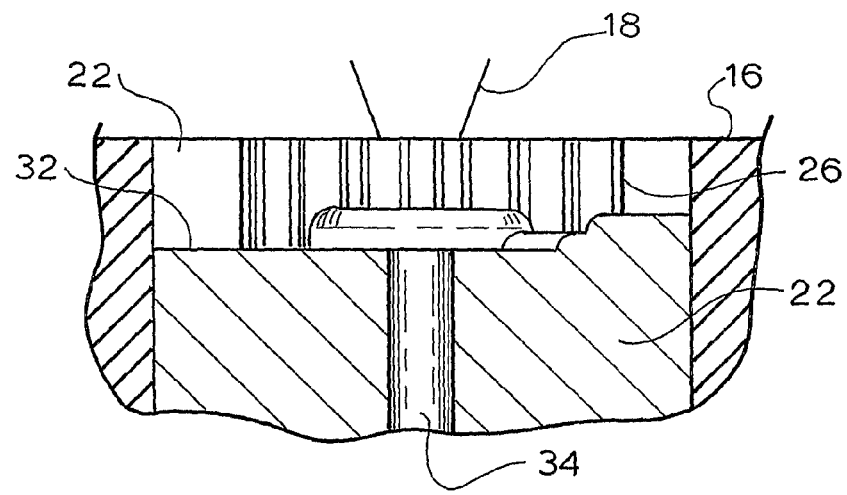
FIG. 3 is a cross-sectional view of the mould cavity of the apparatus of FIG. 1.

FIGS. 1 and 2 illustrate an exemplary molding apparatus 10 in accordance with embodiments of the present invention. As shown, molding apparatus 10 comprises a housing having an upper portion 12 and a lower portion 14 which meet at a parting line 16. The two portions 12, 14 are arranged to be separable and, in certain embodiments, the upper portion 12 is fixed while the lower portion 14 is moveable.

As shown, upper r portion 12 carries an injection nozzle 18 via which moldable electrically insulating material, such as ceramic feedstock, may be injected into a mold cavity 22. Injection nozzle 18 is directed towards an open top end 20 of a mold cavity 22 arranged in lower portion 14 having first and second ends. When upper and lower portions 12, 14 are brought together, a sealing member in the form of an o-ring 24 which provides a vacuum seal which allows a negative pressure to be provided i in cavity 22. As such, injection nozzle 18 is able to inject the ceramic feedstock towards cavity 22.

Figure 5:
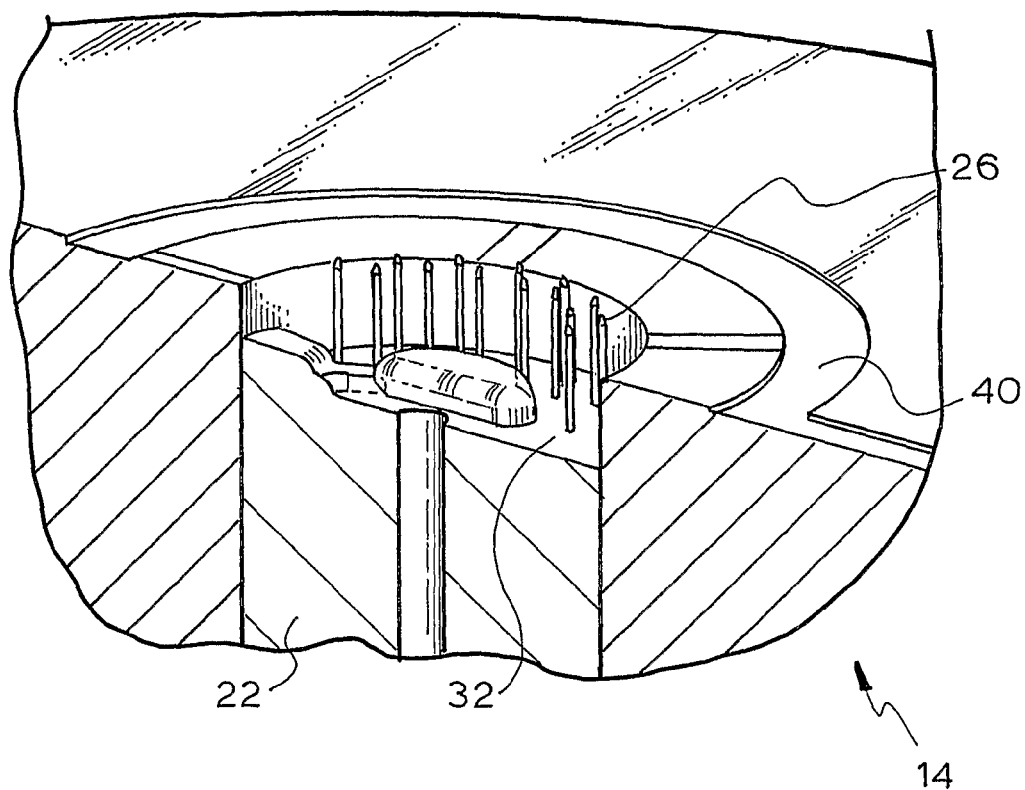
FIG. 5 illustrates the cavity of FIG. 4 in which the cavity member has been removed to expose the cavity, in accordance with embodiments of the present invention.
Figure 6:
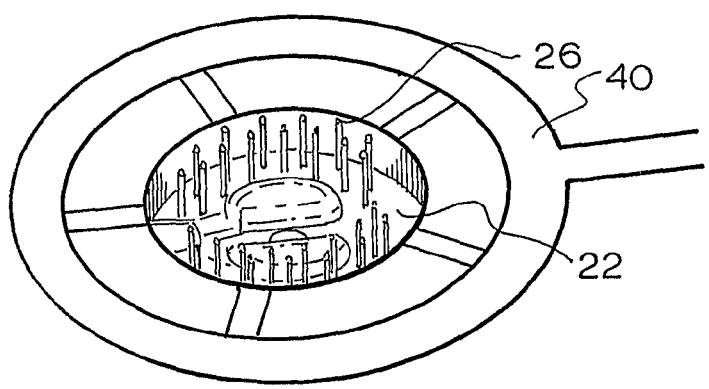
FIG. 6 is a top perspective view of the cavity of FIG. 5.
Figure 7:
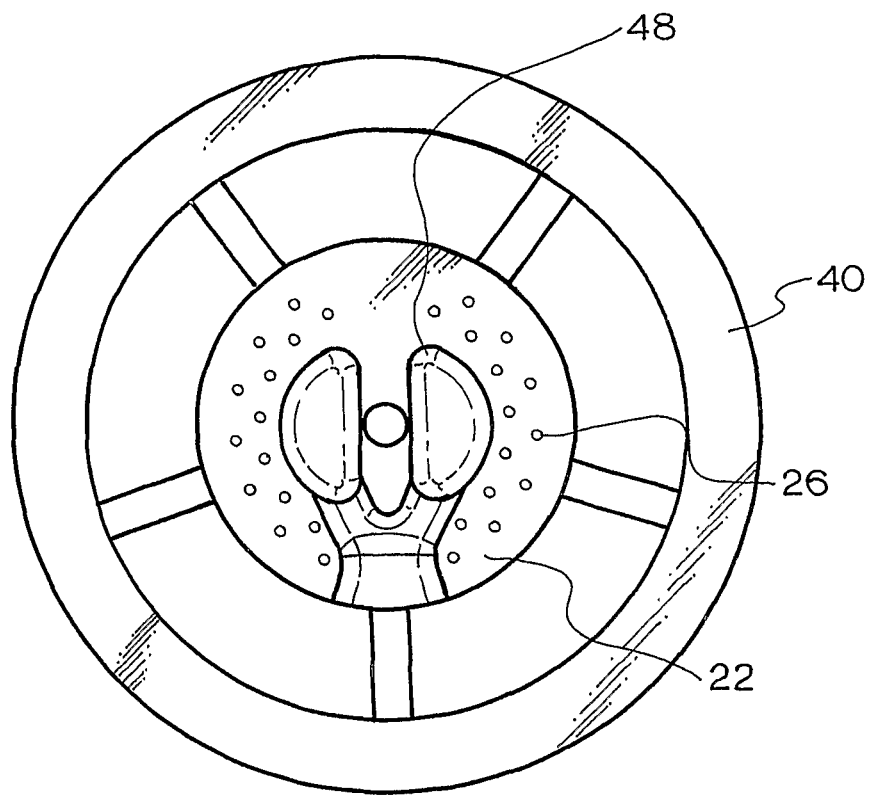
FIG. 7 is a top plane view of the cavity of FIG. 4.

Housed within lower portion 14 and extending through cavity 22 from the second to the first end are a number of pins 26. As shown in FIG. 5, pins 26 extend beyond parting line 16 into upper portion 12. Upper portion 12 is provided with recesses (not shown) which receive the upper ends of pins 26 when portions 12, 14 are brought together.

Figure 4:
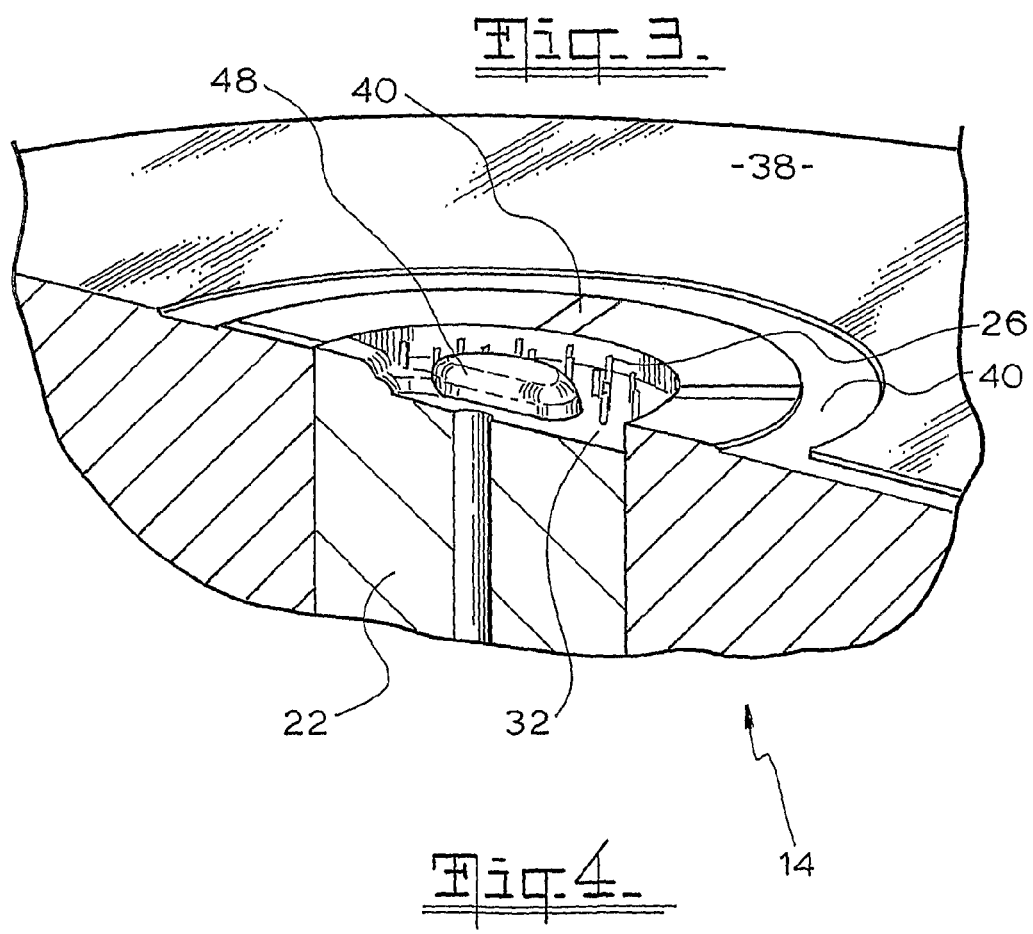
FIG. 4 is a top perspective sectional view of the cavity of FIG. 3 with the cavity member in a biased position, in accordance with embodiments of the present invention.

Arranged within cavity 22 is a moveable cavity member 28 which extends across cavity 22 to define a bounded region of cavity 22, referred to as a sub-cavity. Cavity member 28 is initially biased adjacent the first end (ie. adjacent parting line 16) and is configured to move along a path or axis of travel away from the first end. Cavity member 28 has through-holes through which pins 26 are configured to extend. Cavity member 28 is engaged with a spring-loaded carrier 30 which biases cavity member 28 towards parting line 16, as shown in FIG. 4. When cavity member 28 is biased towards parting line 16, referred to as a biased position, member 28 is substantially close to injection nozzle 18 and only a small portion of each pin 26 is exposed.

When injection nozzle 18 begins injecting the ceramic feedstock, the injected feedstock contacts an upper surface 32 of cavity member 28. Thus, cavity member 28 is positioned adjacent the end of the cavity. The pressure of the injected feedstock causes the cavity member 28 to slide against the spring bias within the cavity 22 and along the length of the pins 26 away from parting line 16. The movement of cavity member 28 away from parting line 16 increases the size of the sub-cavity, i.e. exposes more of cavity 22, and exposes more of the length pins 26 to the injected feedstock. In this manner, the ceramic feedstock gradually fills cavity 22 around the exposed length of pins 26. The gradual exposure of pins 26 by the moving of cavity member 28 prevents damage or deformation of pins 26 due to high injection pressures.

Cavity member 28 is shown having an axial recess 34 within which is arranged an actuator member 36. Actuator member 36 is arranged to engage a pressure sensor (not shown). With this arrangement, the pressure within the cavity 22 can be monitored. In certain embodiments, the pressure sensor is linked in a closed loop arrangement with a controller for the injection process. As such, precise control of injection pressure and holding pressures within cavity 22 is possible. That is, in this embodiment the output of the pressure sensor is used by an injection controller for controlling injection nozzle 18.

As shown in FIGS. 4-7, an upper surface 38 of lower portion 14 is provided with a channel or trench arrangement 40 extending from cavity 22. This trench arrangement 40 allows air to be evacuated from cavity 22 as cavity 22 is filled by the injected ceramic feedstock.

Figure 8:
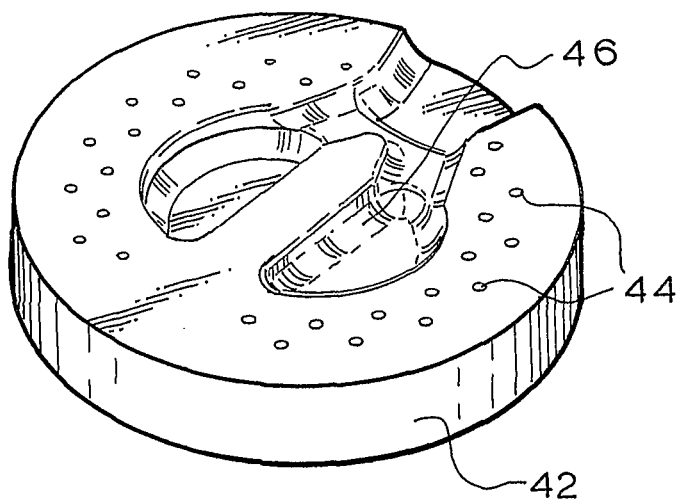
FIG. 8 is a perspective view of a molded structure formed by the apparatus of FIG. 1.
Figure 9:
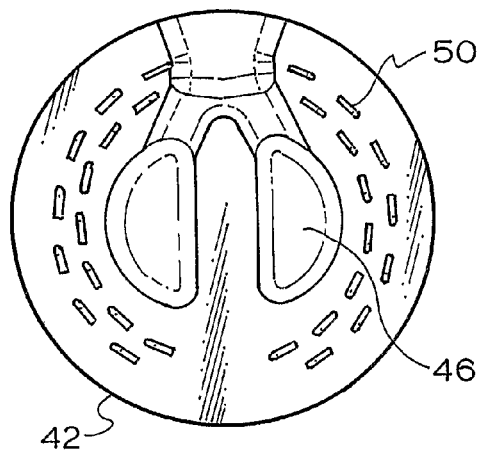
FIG. 9 is a top plan view of the structure of FIG. 8 having conductive members disposed therein, in accordance with embodiments of the present invention.
Figure 10:
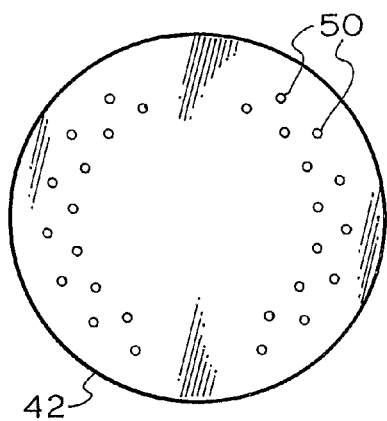
FIG. 10 is a bottom plan view of the structure of FIG. 9.
Figure 11:
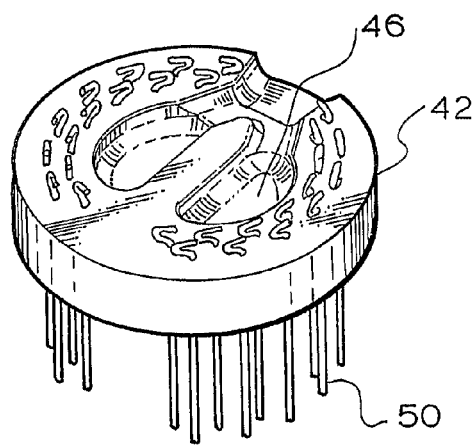
FIG. 11 is a perspective view of the structure of FIG. 9.
Figure 12:
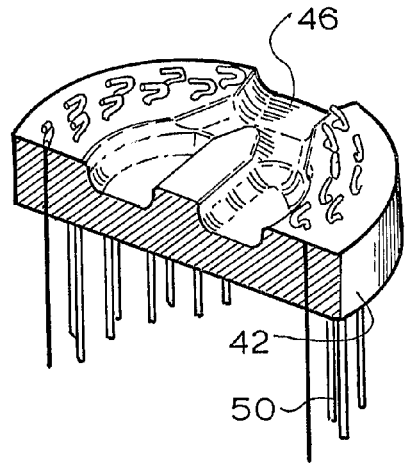
FIG. 12 is a cross-sectional view of the structure of FIG. 11.

Following the above molding process, the molded electrically insulating structure 42 is ejected from cavity 22 while the ceramic is in a green or unsintered state. Resulting structure 42, as shown in FIG. 8, has a disc shape conforming to the shape of cavity 22. Furthermore, structure 42 has through-holes 44 corresponding to where the pins 26 were arranged within cavity 22, and recesses 46 formed on the upper surface thereof. Recesses 46 correspond to the shape of protrusions 48 on cavity member 28 and provide a convenient place for wires for the final feedthrough device.

Following the ejection of structure 42 from cavity 22, the finalized feedthrough device may be formed. Referring to FIGS. 9-12, electrically conductive pins 50 are first inserted into holes 44. In certain embodiments, an automated process is implemented to insert conductive pins 50 into holes 44. However, in other embodiments conductive pins may be manually inserted into holes 44. After insertion of conductive pins 50, structure 42 undergoes a de-binding process. An exemplary de-binding process includes a first a water de-binding step, in which the structure 42 is washed over several hours at approximately 40° C., which is followed by a thermal de-binding step conducted at approximately 300° C. over a period of approximately 24 hours. Finally, structure 42 is sintered at relatively high temperatures of, for example, approximately 1600° C. During the sintering step, ceramic structure 42 shrinks and clamps around conductive pins 50, thereby creating a hermetic seal.

It would be appreciated that a number of different types of ceramic feedstock may be utilized in embodiments of the present invention. However, in embodiments of the present invention, two characteristics influence the choice of suitable ceramic feedstock. A first such characteristic is the ability of a feedstock to shrink during sintering to clamp around conductive pins 50. A second characteristic is the production of a glass phase during sintering which can allow a glaze to form around the conductive pins 50. Two materials having the above characteristics are Alumina and Zirconia. These two materials have a high shrinkage rate, in the range of approximately 16-25 percent. In certain embodiments, composition of the feedstock may include 94-96 percent Alumina ($Al_2O_3$) or Zirconia ($ZrO_2$) with a particle size between approximately 0.5 microns to approximately 3 microns. The composition may also include polyethylene which acts as a binder for the composition. Providing trace amounts of Magnesium oxide, Silicon oxide, Zinc oxide or other oxides may stabilize the ceramic and assist in the formation of the glaze.

If insufficient wall space is provided between conductive pins 50, cracks may form during sintering between the pins 50. As such, as shown in FIGS. 8-12, holes 44 formed in structure 42 for conductive pins 50 may be provided in a staggered configuration to eliminate or substantially reduce the formation of cracks.

In certain embodiments, methods of the present invention utilize a mold apparatus comprising a housing defining a cavity having an axis extending there through, an injection nozzle disposed at a first end of the cavity, a plurality of pins extending through the cavity along the axis, and a cavity member extending across the cavity substantially orthogonal to the axis so as to form a sub-cavity between the cavity member and the first end of the cavity into which the moldable material is injected, the cavity member having a plurality holes through which the pins extend. In such embodiments, the method comprises: biasing the cavity member such that the member is adjacent the first; and injecting moldable electrically insulative material into the cavity via the nozzle such that the cavity member moves, relative to the pins and the housing, along the axis away from the first end to increase the volume of the sub-cavity as the moldable material is injected.

In certain embodiments, the method further includes the step of sealing the mold cavity under vacuum pressure before injecting the feedstock. In exemplary embodiments, the method further includes the step expelling air from the cavity as the feedstock is injected.

In still further embodiments the method includes the step of measuring the pressure within the cavity. In specific such embodiments, the measured pressure is utilized to control the injection of the feedstock.

The invention described and claimed herein is not to be limited in scope by the specific embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the present invention.

The invention claimed is:

1. An apparatus for forming an electrically insulative structure having holes for feedthroughs, comprising:
   a housing defining a cavity having first and second ends;
   an injection nozzle disposed at a first end of the cavity configured to inject moldable material into the cavity;
   a plurality of pins extending through the cavity from the second to the first end; and
   a cavity member extending across the cavity so as to form a sub-cavity between the cavity member and the first end of the cavity into which the moldable material is injected, the cavity member having a plurality of holes through which the pins extend;
   wherein the member is initially positioned such that the member is adjacent the first end, and wherein the member is configured to move, relative to the pins and the housing, away from the first end along an axis to increase the volume of the sub-cavity as the moldable material is injected.

2. The apparatus of claim 1, wherein the apparatus is configured to seal the cavity under vacuum pressure before injecting the moldable material.

3. The apparatus of claim 1, wherein the apparatus comprises at least one channel extending away from the first end of the cavity to allow the expulsion of air from the cavity as the moldable material is injected.

4. The apparatus of claim 1, wherein a portion of the housing surrounding the injection nozzle comprises a plurality of holes to receive ends of the pin.

5. The apparatus of claim 1, further comprising:
   a spring member configured to initially bias the cavity member adjacent the first end.

6. The apparatus of claim 1, further comprising:
   a pressure sensor arranged to determine the pressure within the cavity.

7. The apparatus of claim 6, wherein the apparatus is configured to utilize the output of the pressure sensor to control the flow of material from the injection nozzle.

8. The apparatus of claim 1, wherein the movement of the member to increase the volume of the sub-cavity exposes more of a length of the pins within the cavity.

9. An apparatus for forming an electrically insulative structure having holes for feedthroughs, comprising:
   upper and lower portions defining a cavity having first and second ends;
   an injection nozzle disposed in the upper portion configured to inject moldable material into the cavity;
   a plurality of pins extending through the cavity along the axis;
   a cavity member extending across the cavity substantially so as to form a sub-cavity between the cavity member and the first end of the cavity into which the moldable material is injected, the cavity member having a plurality of holes through which the pins extend;
   wherein the member is initially positioned such that the member is adjacent the first end, and wherein the member is configured to move, relative to the pins and the housing, along an axis to increase the volume of the sub-cavity as the moldable material is injected.

10. The apparatus of claim 9, wherein the apparatus is configured to seal the cavity under vacuum pressure before injecting the moldable material.

11. The apparatus of claim 9, wherein the apparatus comprises at least one channel extending away from the first end of the cavity to allow the expulsion of air from the cavity as the moldable material is injected.

12. The apparatus of claim 9, wherein the upper portion of the housing surrounding the injection nozzle comprises a plurality of holes to receive the ends of the pins.

13. The apparatus of claim 9, further comprising:
   a spring member configured to initially bias the cavity member adjacent the first end.

14. The apparatus of claim 9, further comprising:
   a pressure sensor arranged to determine the pressure within the cavity.

15. The apparatus of claim 14, wherein the apparatus is configured to utilize the output of the pressure sensor to control the flow of material from the injection nozzle.

16. The apparatus of claim 9, wherein the movement of the member to increase the volume of the sub-cavity exposes more of a length of the pins within the cavity.

* * * * *